United States Patent [19]

Kitamura et al.

[11] Patent Number: 4,968,793
[45] Date of Patent: Nov. 6, 1990

[54] PROCESS FOR PRODUCING ε-CAPROLACTAM

[75] Inventors: Masaru Kitamura; Hiroshi Ichihashi; Gohfu Suzukamo; Yasuo Nakamura, all of Osaka, Japan

[73] Assignee: Sumitomo Chemical Company, Limited, Osaka, Japan

[21] Appl. No.: 468,935

[22] Filed: Jan. 23, 1990

[30] Foreign Application Priority Data

Jan. 26, 1989 [JP] Japan ................................. 1-19242
Mar. 23, 1989 [JP] Japan ................................. 1-73057

[51] Int. Cl.$^5$ .......................................... C07D 201/04
[52] U.S. Cl. ................................................... 540/536
[58] Field of Search ........................................ 540/536

[56] References Cited

U.S. PATENT DOCUMENTS 4,359,421 11/1982 Bell et al. ............................ 540/536
4,709,024 11/1987 Sato et al. ........................... 540/536
4,717,769 1/1988 Sato et al. ........................... 540/536
4,717,770 1/1988 Sato et al. ........................... 540/536

OTHER PUBLICATIONS

"New Developments . . . ", Describes a Gas Phase Beckmann Rearrangement with ZSM-5 Zeolite with Respect to 1, Catalyst Activity, Selectivity and Life Rely on Si/AL Atomic Ratio of ZSM-5, and 2, H.ZSM-5 or Silicate Where Si/AL atomic ratio is 1000 or more gives a good result.

*Primary Examiner*—Robert T. Bond
*Attorney, Agent, or Firm*—Cushman, Darby & Cushman

[57] ABSTRACT

ε-caprolactam is produced by gas phase reaction of cyclohexanone oxime using a solid acid as a catalyst in the presence of a compound represented by the formula (I): $R_1$—O—$R_2$ (wherein $R_1$ represents a lower alkyl group which may be substituted with a fluorine atom and $R_2$ represents a hydrogen atom, a lower alkyl group or a phenyl group) such as a lower alcohol or an ether compound. The solid acid includes a crystalline metallosilicate or a crystalline silicate.

16 Claims, No Drawings ically, use of one or more of the ether compounds having methyl group as $R_1$ results in remarkable effect for improvement of selectivity of ε-caprolactam and life of catalyst and thus these are more preferred.

PROCESS FOR PRODUCING ε-CAPROLACTAM

BACKGROUND OF THE INVENTION

The present invention relates to a process for producing ε-caprolactam from cyclohexanon oxime using a solid acid as a catalyst under conditions of gas phase reaction.

ε-caprolactam is an important raw material for nylon and the like. One of the processes for producing the caprolactam is liquid phase rearrangement of cyclohexanone oxime using fuming sulfuric acid or concentrated sulfuric acid as a catalyst.

However, the above process has the problems that a large amount of fuming sulfuric acid is required and besides ammonium sulfate is by produced in a large amount.

As an approach to solve these problems, various processes have been proposed according to which cyclohexanone oxime is rearranged in gas phase using a solid acid as a catalyst. For example, there has been proposed use of boric acid catalyst (Japanese Published Unexamined Patent Application No. 37686/78 and Japanese Published Examined Application No. 12125/71), silica alumina catalysts (British Patent No. 831,927), solid phosphoric acid catalyst (British Patent No. 881,926), mixed metal oxide catalysts (Journal of the Chemical Society of Japan, No. 1, 77, 1977), and zeolite catalysts (Journal of Catalysis, 6, 247, 1966 and U.S. Pat. No. 4,359,421.

However, the above processes have problems in reaction selectivity of the objective ε-caprolactam, life of catalysts, productivity per catalyst and quality of the product ε-caprolactam. For example, U.S. Pat. No. 4,359,421 discloses an example of using a crystalline zeolite such as ZSM-5 having an atomic ratio of Si/Al of 40-60 and mentions that conversion of cyclohexanone oxime is quantitative, but is silent about selectivity of ε-caprolactam. Besides, it shows a short catalyst life of 15-20 hours. The present inventors have also studied use of ZSM-5 zeolite having the Si/Al atomic ratio as mentioned in the above patent and have found that not only the life of catalyst, but the selectivity of ε-caprolactam are not enough.

U.S. Pat. Nos. 4,709,024 and 4,717,769 show use of a crystalline aluminosilicate having an Si/Al atomic ratio of at least 500 and an acid amount on external surface of less than a specific value and a crystalline metallosilicate having an Si/metal atomic ratio of at least 500. Selectivity of these catalysts has been considerably improved as compared with conventional silica catalysts. Furthermore, U.S. Pat. No. 4,717,770 discloses that when crystalline zeolite catalysts are surface treated with an organometallic compound, selectivity can be improved.

SUMMARY OF THE INVENTION

An ojbect of the present invention is to provide a process according to which ε-caprolactam can be produced with very high selectivity even under conditions of conversion rate of cyclohexanone oxime being, for example, substantially around 100% by allowing a specific compound to be present together with cyclohexanone oxime in the reaction system.

Another object of the present invention is to provide a process for producing ε-caprolactam wherein life of catalyst is improved than in conventional processes.

That is, the present invention provides a process for producing ε-caprolactam from cyclohexanone oxime under conditions of gas phase reaction using a solid acid as a catalyst, characterized in that a compound represented by the formula: $R_1-O-R_2$ (I) (wherein $R_1$ represents a lower alkyl group which may be substituted with fluorine atom and $R_2$ represents a hydrogen atom, a lower alkyl group or a phenyl group) is present in the reaction system.

DESCRIPTION OF THE INVENTION

The present invention will be explained in detail.

In the present invention a solid acid is used as a catalyst The solid acid is preferably a silicon oxide-containing catalyst, especially crystalline metallosilicate. More preferably, the crystalline metallosilicate has an Si/Me atomic ratio (wherein Me represents at least one metallic element selected from Al, Ga, Fe, B, Zn, Cr, Be, Co, La, Ti, Zr, Hf, V, Ni, Sb, Bi, Cu, Nb, and the like) of at least 5. A crystalline silicate comprising silicon dioxide containing substantially no Me component is also preferred.

The Si/Me ratio can be obtained by usual analytical means such as atomic absorption spectrometry and X-ray fluorescence analysis.

These catalysts are prepared by known processes. These crystalline metallosilicate and crystalline silicate are known to have various crystal forms and especially preferred are those which belong to so-called pentasil type structure.

In the present invention, a compound represented by the formula $R_1-O-R_2$ (I) (wherein $R_1$ represents a lower alkyl group which may be substituted with a fluorine atom and $R_2$ represents a hydrogen atom, a lower alkyl group or a phenyl group) is present in the reaction system.

As examples of $R_1$ in the formula, mention may be made of lower alkyl groups of 1-6 carbon atoms which may be substituted with fluorine atom such as methyl, ethyl, propyl, butyl, amyl, hexyl, monofluoroethyl, difluoroethyl, trifluoroethyl, and hexafluoroisopropyl.

Examples of $R_2$ in the formula include a hydrogen atom, lower alkyl groups of 1-6 carbon atoms such as methyl, ethyl, propyl, butyl, amyl and hexyl, and a phenyl group.

As examples of the compounds represented by the formula (I), mention may be made of lower alcohols having hydrogen atom as $R_2$ and ether compounds having lower alkyl group or phenyl group as $R_2$.

As the lower alcohols, there may be used, for example, one or more of methanol, ethanol, n-propanol, isopropanol, n-butanol, sec-butanol, isobutanol, n-amyl alcohol, n-hexanol, and 2,2,2-trifluoroethanol. Especially, use of one or more of methanol, ethanol, n-propanol, isopropanol, and n-butanol results in remarkable effect for improvement of selectivity of ε-caprolactam and life of catalyst and thus these are more preferred. Methanol and ethanol are especially preferred because of their remarkable effect and from industrial viewpoint.

As the ether compounds, there may be used, for example, one or more of dimethyl ether, methyl ethyl ether, diethyl ether, methyl n-propyl ether, methyl isopropyl ether, methyl tert-butyl ether and anisole. Especially, use of one or more of the ether compounds having methyl group as $R_1$ results in remarkable effect for improvement of selectivity of ε-caprolactam and life of catalyst and thus these are more preferred.

Usually, the process of the present invention is carried out under atmospheric pressure or reduced pressure lower than atmospheric pressure.

Method for reaction in practice of the present invention will be explained.

Reaction is carried out by gas phase catalytic method in a fixed-bed or fluidized bed. The starting material cyclohexanone oxime is brought in the gas form into contact with catalyst bed. On the other hand, the lower alcohol or ether compound can be previously mixed in the gas phase with cyclohexanone oxime or can be fed to a reactor separately from cyclohexanone oxime. In case of fixed-bed, it is preferred to pass cyclohexanone oxime and lower alcohol or ether compound which are well mixed with each other through catalyst bed. In case of fluidized bed, cyclohexanone oxime and lower alcohol or ether compound are not always necessarily previously mixed and can be separately fed from each other and besides, lower alcohol or ether compound can be divisionally added. Furthermore, in case of fluidized bed, lower alcohol or ether compound may be added at the position upstream the position of addition of cyclohexanone oxime.

Amount of lower alcohol to be present in the reaction system is normally 0.1–20 times, preferably 10 times or less, more preferably 0.3–8 times as much as the weight of cyclohexanone oxime.

Amount of ether compound to be present in the reaction system is suitably 0.1–20 times, more preferably 0.3–15 times as much as the weight of cyclohexanone oxime.

In the present invention, vapor of a compound inert to the reaction such as benzene, cyclohexane or toluene or an inert gas such as nitrogen or carbon dioxide may be present as a diluent gas in the reaction system.

Reaction temperature may usually be within the range of 250°–500° C. If the reaction temperature is lower than 250° C., reaction rate is not sufficient and selectivity of ε-caprolactam tends to decrease. If it is higher than 500° C., selectivity of ε-caprolactam tends to decrease since thermal decomposition of cyclohexanone oxime cannot be ignored. Especially preferred range is 300°–450° C., and most preferred is 300°–400° C.

Space velocity (WHSV) of the starting material cyclohexanone oxime is 0.1–40 $hr^{-1}$ (i.e., feeding speed of cyclohexanone oxime per 1 kg of catalyst is 0.1–40 kg/hr). It is preferably 0.2–20 $hr^{-1}$, more preferably 0.5–10 $hr^{-1}$.

Isolation of ε-caprolactam from reaction mixture can be carried out by customary method. For example, ε-caprolactam can be obtained by cooling and condensing the reaction mixture gas and then purifying it by extraction, distillation, crystallization or the like.

Lower alcohol or ether compound added to the rearrangement reaction system can be recovered from reaction mixture and reused.

Catalyst reduced in activity due to long-term use thereof can be easily activated to the original activity by calcining it in a gas stream containing oxygen gas and thus can be repeatedly used.

As explained in detail above, according to the present invention, ε-caprolactam can be produced with very high selectivity even under the conditions where the conversion of cyclohexanone oxime is substantially about 100% and in addition the life of catalyst can be markedly improved than by conventional processes. Besides, alcohol or ether compound added to the reaction system can be recovered and used repeatedly.

The following nonlimiting examples further illustrate the present invention.

Reference Example 1 (Preparation of catalyst A)

Tetraethylorthosilicate ($Si(OC_2H_5)_4$, 100 g, Al content $\leq$ 10 ppm), 224.0 g of 10% aqueous solution of tetra-n-propylammonium hydroxide and 214 g of ethanol were charged in a 1.5 liter stainless steel autoclave and vigorously stirred for 30 minutes. The mixed solution had a pH of 13. The autoclave was tightly sealed and then dipped in an oil bath to keep the internal temperature at 105° C. Hydrothermal synthesis was carried out for 120 hours with stirring at least 400 r.p.m. Pressure in the autoclave reached 2–3 $kg/cm^2$. PH at completion of the hydrothermal synthesis was 11.8. A white solid product was filtered off and washed continuously with distilled water until pH of filtrate reached about 7. The white solid was dried and then was calcined at 500°–530° C. for 4 hours in air stream to obtain 27 g of powdery white crystals, The crystals were identified to be pentasil type zeolite by powder X-ray diffraction. Si/Al atomic ratio was 147000 according to atomic absorption spectroscopy assay.

To 10 g of the crystals was added 100 g of 5% aqueous ammonium chloride solution to carry out ion exchange treatment at 50°–60° C. for 1 hour and then the crystals were filtered off. This ion exchange treatment was carried out four times and then the crystals were washed with distilled water until no $Cl^-$ was detected and subsequently dried at 120° C. for 16 hours. The thus obtained crystals of $NH_4$ form were shaped to particles of 24–48 mesh and then calcined at 500° C. for 1 hour in a nitrogen gas stream to obtain catalyst A.

Reference Example 2 (Preparation of catalyst B)

Tetraethylorthosilicate ($Si(OC_2H_5)_4$, 100 g), 224 g of 10% aqueous solution of tetra-n-propylammonium hydroxide and 60 g of ethanol were charged in a 1.5 liter stainless steel autoclave and sufficiently sirred. To this mixed solution was added 48 g of previously prepared aqueous aluminum sulfate solution ]$Al_2(SO_4)_3 \cdot 18H_2O$ 20 mg/water 48 g], followed by vigorous stirring for 30 minutes. The mixed solution had a pH of 13. The autoclave was tightly sealed and then dipped in an oil bath to keep the internal temperature at 105° C. Hydrothermal synthesis was carried out for 120 hours with stirring by revolution of at least 400 r.p.m. Pressure in the autoclave reached 2–3 $kg/cm^2$. PH at completion of the hydrothermal synthesis was 11.8. A white solid product was calcined in the same manner as in Reference Example 1 to obtain powdery white crystals. The crystals were identified to be pentasil type zeolite by powder X-ray diffraction. Si/Al atomic ratio was 7000 according to atomic absorption spectroscopy assay.

Thereafter, the crystals were subjected to ion exchange treatment and calcined in the same manner as in Reference Example 1 to obtain catalyst B.

Reference Example 3 (Preparation of catalyst C)

Solution of raw materials having the following compositions were prepared.

Solution A: Distilled water: 162 g; Sulfuric acid: 16.7 g; $Al_2(SO_4)_3 \cdot 18H_2O$: 2.92 g; (n-Pr)$_4$NBr: 20.8 g Solution B: Distilled water: 119.7 g; No. 3 Sodium silicate: 186.3 g Solution C: Distilled water: 281.7 g; Sodium chloride: 70.7 g Solutions A and B were simultaneously added dropwise to solution C with vigorous stirring and were mixed. PH at completion of the mixing was 9.6. The mixture was charged in a 1.5 liter stainless steel autoclave. Hydrothermal synthesis was carried out for 20 hours at 160° C. with stirring at least 400 r.p.m. After cooling, filtration and sufficient washing with about 7 liter of distilled water were repeated until no Cl− ion was detected. The resulting white solids were dried at 120° C. for 16 hours. Then, the crystals were calcined at 500°-550° C. for 4 hours in air stream to obtain white powdery crystals. The crystals were identified to be pentasil type zeolite by powder X-ray diffraction. Si/Al atomic ratio was 50 according to atomic absorption spectroscopy assay.

Thereafter, the crystals were subjected to ion exchange treatment and calcined in the same manner as in Reference Example 1 to obtain catalyst C.

Reference Example 4 (Preparation of catalyst D)

Solution of raw materials having the following compositions were prepared.

Solution A: Distilled water: 443 g; Sulfuric acid: 45 g; (n-Pr)$_4$NBR: 55.8 g

Solution B: Distilled water: 320 g; No. 3 Sodium silicate: 453 g

Solution C: Distilled water: 754 g; Sodium chloride: 189 g

Solutions A and B were simultaneously added dropwise to solution C with vigorous stirring and were mixed. PH at completion of the mixing was 9.5. The mixture was charged in a 3 liter stainless steel autoclave. Hydrothermal synthesis was carried out for 20 hours at 160° C. with stirring at least 350 r.p.m. After cooling, filtration and sufficient washing with about 15 liter of distilled water were repeated until no Cl− ion was detected. The resulting white solids were calcined in the same manner as in Reference Example 1 to obtain white powdery crystals. The crystals were identified to be pentasil type zeolite by powder X-ray diffraction. Si/Al atomic ratio was 100 according to atomic absorption spectroscopy assay.

Thereafter, the crystals were subjected to ion exchange treatment and calcined in the same manner as in Reference Example 1 to obtain catalyst D.

Reference Example 5 (Preparation of catalyst E)

Solutions of raw materials having the following compositions were prepared.

Solution A: Distilled water: 150 g; (n-Pr)$_4$NBr: 81 g; Colloidal silica (SI-30): 118.8 g Solution B: Distilled water: 150 g; Sodium hydroxide: 76.5 g Solution B was added dropwise to solution A and mixed. The mixture was charged in a 1 liter stainless steel autoclave and hydrothermal synthesis was carried out for 24 hours at 160° C. with stirring. After cooling, the product was filtered off and continuously washed with distilled water until pH of filtrate reached about 7.

The resulting white solids were calcined in the same manner as in Reference Example 1 to obtain powdery crystals. The crystals were identified to be pentasil type zeolite by powder X-ray diffraction. Si/Ai atomic ratio was 1400 according to atomic absorption spectroscopy assay.

Thereafter, the crystals were subjected to ion exchange treatment and calcination in the same manner as in Reference Example 1 to obtain catalyst E.

Reference Example 6 (Preparation of catalyst F)

In a 1.5 liter stainless steel autoclave were charged 217.5 g of 10% aqueous solution of tetra-n-propylammonium hydroxide, 214 g of ethanol, 2 ml of aqueous solution containing 64.2 mg of zirconium oxynitrate and 100 g of high purity tetraethylorthosilicate (Si-(OC$_2$H$_5$)$_4$) in this order, followed by sufficient stirring for 1 hour. The internal temperature was kept at 105°C. and hydrothermal synthesis was carried out for 48 hours with stirring at least 400 r.p.m. The resulting white solid product was filtered off and washed continuously with distilled water until pH of filtrate reached about 7. The crystals were dried at 120° C. for 16 hours. The dried crystals were calcined at 500°-550° C. for 4 hours in air stream to obtain 27 g of powdery white crystals. The crystals were identified to be zirconosilicate having structure similar to pentasil type zeolite by powder X-ray diffraction. Si/Zr atomic ratio was 2400 according to atomic absorption spectroscopy assay.

Thereafter, the crystals were subjected to ion exchange treatment and calcination in the same manner as in Reference Example 1 to obtain catalyst F.

Reference Example 7 (Preparation of catalyst G)

White crystals were obtained by hydrothermal synthesis, filtration and calcination in the same manner as in Reference Example 6 except that 1.414 g of titanium tetraisopropoxide was used in place of the zirconium oxynitrate. The crystals were identified to be crystalline silicate having the structure similar to that of pentasil type zeolite by powder X-ray diffraction. Si/Ti atomic ratio was 90 according to atomic absorption spectroscopy assay. Subsequently, the crystals were subjected to ion exchange treatment and calcination in the same manner as in Reference Example 1 to obtain catalyst G.

Reference Example 8 (Preparation of catalyst H)

White crystals were obtained by hydrothermal synthesis, filtration and calcination in the same manner as in Reference Example 6 except that 30.2 mg of vanadium trichloride was used in place of the zirconium oxynitrate. The crystals were identified to be crystalline silicate having structure similar to that of pentasil type zeolite by powder X-ray diffraction. Si/V atomic ratio was 2300 according to atomic absorption spectroscopy assay. Then, the crystals were subjected to the same ion exchange treatment and calcination as in Reference Example 1 to obtain catalyst H.

Reference Example 9 (Preparation of catalyst I)

Aerosil (amorphous silica of high purity, 45.0 g), 45.73 g of tetra-n-propylammonium bromide, 10.8 g of sodium hydroxide and 375.81 g of distilled water were charged in a 1.5 liter stainless steel autoclave. The autoclave was tightly sealed, followed by vigorous stirring at 20° C. for 120 hours. The mixed solution had a pH of 12.8. The internal temperature was kept at 105° C. and hydrothermal synthesis was carried out for 96 hours with stirring at least 400 r.p.m. A white solid product was filtered off and washed continuously with distilled water until pH of filtrate reached about 7. The white solid product was calcined in the same manner as in Reference Example 1 to obtain white powdery crystals. The crystals were identified to be pentasil type zeolite by powder X-ray diffraction. Si/Al atomic ratio was 360 according to atomic absorption spectroscopy assay.

Thereafter, the crystals were subjected to ion exchange treatment and calcination in the same manner as in Reference Example 1 to obtain catalyst I.

Reference Example 10 (Preparation of catalyst J)

Tetraethylorthosilicate (Si(OC$_2$H$_5$)$_4$, 104.17 g), 232.85 g of 10% aqueous solution of tetra-n-propylammonium hydroxide, 62.33 g of ethanol, and 50.44 g of distilled water were charged in a 1.5 liter stainless steel autoclave and vigorously stirred for 30 minutes. The mixed solution had a pH of 12.5. The autoclave was tightly sealed and then dipped in an oil bath to keep the internal temperature at 105° C. Hydrothermal synthesis was carried out for 96 hours with stirring at least 400 r.p.m. Pressure in the autoclave reached 2–3 kg/cm$^2$. PH at completion of the hydrothermal synthesis was 11.7. A white solid product was calcined in the same manner as in Reference Example 1 to obtain white powdery crystals. The crystals were identified to be pentasil type zeolite by powder X-ray diffraction. Si/Al atomic ratio was 9000 according to atomic absorption spectroscopy assay.

The crystals were subjected to ion exchange treatment and calcination in the same manner as in Reference Example 1 to obtain catalyst J.

EXAMPLE 1

Catalyst A (0.3 g, 0.5 ml) was packed in a quartz glass reaction tube of 1 cm in inner diameter and was preheated in a nitrogen stream at 350° C. for 1 hour. Then, a mixed solution of cyclohexanone oxime/methanol/benzene = 1/2.3/11.5 (weight ratio) was fed to the reaction tube at a feeding rate of 11.5 g/hr to carry out reaction. Space velocity WHSV was 2.6 hr$^{-1}$ and temperature of catalyst bed (reaction temperature) was 350° C. Reaction product was trapped and collected under water-cooling every one hour and analyzed by gas chromatography.

Methanol was recovered at recovery of at least 98% in all analyses.

The resutls are shown in Table 1.

TABLE 1

| Time lapsed (hr) | Conversion (%) | Selectivity (%) |
|---|---|---|
| 1.25 | 99.4 | 89.2 |
| 3.25 | 99.0 | 92.3 |
| 6.25 | 98.7 | 91.2 |

The space velocity WHSV is the value calculated by the following formula and conversion of cyclohexanone oxime and selectivity of ε-caprolactam are calculated by the following formulas, respectively.

WHSV (hr$^{-1}$) = feeding rate of cyclohexanone oxime (kg/hr)/weight of catalyst (kg)

Coversion (%) of cyclohexanone oxime = {(X − Y)/X} × 100
Conversion (%) of cyclohexanone oxime = {(X-Y)/X}x 100 Selectivity (%) of ε-caprolactam = {Z/(X-Y)}x 100

In the above formulas, X, Y and Z are as follows:
X = Mol number of the starting cyclohexanone oxime fed
Y = Mol number of unaltered cyclohexanone oxime
Z = Mol number of ε-caprolactam in the product

EXAMPLES 2–8

The catalysts obtained in the reference examples were respectively subjected to preheating treatment in the same manner as in Example 1 and reactions were carried out using 0.3 g (0.5 ml) of each of the preheated catalysts at the same weight ratio of cyclohexanone oxime/methanol/benzene, feeding rate of the mixed solution and reaction temperature as in Example 1. Results of the reaction are shown in Table 2.

TABLE 2

| Example | Catalyst | WHSV (hr$^{-1}$) | Time lapsed (hr) | Conversion (%) | Selectivity (%) |
|---|---|---|---|---|---|
| 2 | B | 2.7 | 2.25 | 99.4 | 87.4 |
|   |   |     | 6.25 | 98.0 | 87.8 |
| 3 | C | 2.6 | 2.25 | 80.9 | 78.2 |
|   |   |     | 6.25 | 44.8 | 75.0 |
| 4 | D | 2.6 | 1.25 | 97.5 | 81.6 |
|   |   |     | 6.25 | 73.2 | 79.5 |
| 5 | E | 2.6 | 1.25 | 97.8 | 84.6 |
|   |   |     | 6.25 | 90.6 | 84.5 |
| 6 | F | 2.8 | 1.25 | 99.8 | 95.5 |
|   |   |     | 3.25 | 99.8 | 95.4 |
| 7 | G | 2.7 | 1.25 | 98.2 | 83.3 |
|   |   |     | 6.25 | 91.7 | 84.8 |
| 8 | H | 2.6 | 3.25 | 91.1 | 89.0 |
|   |   |     | 6.25 | 88.4 | 92.2 |

Comparative Examples 1–8

Example 1 was repeated except that methanol was not present in the reaction system and a mixed solution of cyclohexanone oxime/benzene = 1/11.5 (weight ratio was fed to the reaction tube at a feeding rate of 11.5 g/hr and reaction was carried out at 350 ° C.

The results are shown in Table 3.

TABLE 3

| Comparative Example | Catalyst | WHSV (hr$^{-1}$) | Time lapsed (hr) | Conversion (%) | Selectivity (%) |
|---|---|---|---|---|---|
| 1 | A | 3.1 | 3.25 | 100 | 79.6 |
|   |   |     | 6.25 | 97.8 | 81.3 |
| 2 | B | 3.1 | 1.25 | 99.8 | 78.1 |
|   |   |     | 6.25 | 89.7 | 81.8 |
| 3 | C | 3.3 | 2.25 | 16.8 | 55.8 |
|   |   |     | 6.25 | 8.0 | 43.9 |
| 4 | D | 3.1 | 1.25 | 96.4 | 62.6 |
|   |   |     | 6.25 | 39.1 | 72.4 |
| 5 | E | 3.1 | 1.25 | 89.5 | 70.2 |
|   |   |     | 5.25 | 67.9 | 70.1 |
| 6 | F | 3.1 | 1.25 | 100 | 82.9 |
|   |   |     | 6.25 | 98.3 | 88.2 |
| 7 | G | 3.1 | 1.25 | 100 | 74.6 |
|   |   |     | 6.25 | 87.7 | 81.5 |
| 8 | H | 3.1 | 3.25 | 100 | 83.9 |
|   |   |     | 6.25 | 96.9 | 84.8 |

EXAMPLE 9

In order to confirm reproducibility of catalyst preparation and rearrangement reaction of cyclohexanone oxime, a catalyst was prepared in the same manner as in preparation of catalyst A in Reference Example 1. (The obtained catalyst was referred to as "catalyst A*" hereinafter. Si/Al atomic ration was 147000.). Using 0.3 g (0.5 ml) of catalyst A*, reaction was carried out under the same conditions as in Example 1. The results are shown in Table 4.

TABLE 4

| Time lapsed (hr) | Conversion (%) | Selectivity (%) |
|---|---|---|
| 1.25 | 99.1 | 90.4 |
| 4.25 | 98.4 | 90.7 |
| 6.25 | 97.8 | 89.5 |

Comparative Example 9

Reaction was carried out under the same conditions as in Comparative Example 1 in the absence of methanol in the reaction system using catalyst A* in the same amount as in Example 9.

The results are shown in Table 5.

TABLE 5

| Time lapsed (hr) | Conversion (%) | Selectivity (%) |
|---|---|---|
| 1.25 | 100 | 75.6 |
| 4.25 | 99.5 | 78.0 |
| 6.25 | 98.6 | 77.4 |

EXAMPLE 10

Reaction was carried out under the same conditions as in Example 1 except that benzene was not present in the reaction system, using the same amount of catalyst A* as in Example 9 by feeding a mixed solution of cyclohexanone oxime/methanol=1/2 (weight ratio) to the reaction tube at a feeding rate of 3.0 g/hr. WhsV was 3.3 hr$^{-1}$ and reaction temperature was 350° C.

The results are shown in Table 6.

TABLE 6

| Time lapsed (hr) | Conversion (%) | Selectivity (%) |
|---|---|---|
| 1.25 | 99.7 | 87.7 |
| 3.25 | 99.6 | 85.5 |
| 6.25 | 99.7 | 86.3 |

EXAMPLE 11

As in Example 10, in the absence of benezene, reaction was carried out, using the same amount of catalyst A* as in Example 9 by feeding a mixed solution of cyclohexanone oxime/methanol=1/13 (weight ratio) to a reaction tube at a feeding rate of 11.7 g/hr. WHSV was 2.8 hr$^{-1}$ and reaction temperature was 350° C.

The results are shown in Table 7

TABLE 7

| Time lapsed (hr) | Conversion (%) | Selectivity (%) |
|---|---|---|
| 1.25 | 63.3 | 84.2 |
| 6.25 | 36.5 | 86.3 |

EXAMPLES 12-≠

Reaction was carried out at the same feeding rate and reaction temperature as in Example 1 except that catalyst A* was used in the same amount as in Example 9 and alcohols as shown in Table 8 were used in place of the methanol.

The results are shown in Table 8.

TABLE 8

| Example | Alcohol | Feeding[1] ratio | WHSV (hr$^{-1}$) | Time lapsed (hr) | Conversion (%) | Selectivity (%) |
|---|---|---|---|---|---|---|
| 12 | Ethanol | 1/1.6/9.9 | 3.1 | 2.25 | 99.0 | 91.8 |
|  |  |  |  | 6.25 | 99.0 | 91.2 |
| 13 | n-Propanol | 1/2.0/9.5 | 2.9 | 1.25 | 96.6 | 90.4 |
|  |  |  |  | 6.25 | 92.6 | 91.9 |
| 14 | Iso-propanol | 1/2.0/9.5 | 2.9 | 1.25 | 99.8 | 87.9 |
|  |  |  |  | 4.25 | 99.5 | 91.8 |
| 15 | n-Hexanol | 1/7.3/6.5 | 2.6 | 1.25 | 59.8 | 87.2 |
|  |  |  |  | 3.25 | 40.2 | 82.1 |
| 16 | 2,2,2-Trifluoro ethanol | 1/7.1/6.7 | 2.6 | 1.25 | 99.8 | 86.4 |
|  |  |  |  | 3.25 | 99.3 | 87.4 |

Note:
[1]Ratio of cyclohexanone oxime/alcohol/benzene (weight)

EXAMPLES 17-18

Reaction was carried out at the same feeding rate and reaction temperature as in Example 1, using catalyst A* in the same amount as in Example 9 with changing the feed ratio of cyclohexanone oxime/methanol/benzene (weight).

The results are shown in Table 9.

TABLE 9

| Example | Feeding[1] ratio | WHSV (hr$^{-1}$) | Time lapsed (hr) | Conversion (%) | Selectivity (%) |
|---|---|---|---|---|---|
| 17 | 1/0.5/11.0 | 3.1 | 1.25 | 99.8 | 83.4 |
|  |  |  | 6.25 | 99.0 | 86.6 |
| 18 | 1/1.1/12.6 | 2.6 | 1.25 | 100 | 90.9 |
|  |  |  | 6.25 | 99.6 | 90.9 |

Note:
[1]Ratio of cyclohexanone oxime/methanol/benzene (weight)

EXAMPLE 19

Catalyst A* (0.5 g, 0.8 ml) was packed in a quartz glass reaction tube of 1 cm in inner diameter and was preheated as in Example 1. Then, a mixed solution of cyclohexanone oxime/methanol/benezene=1/1.1/10.4 (weight ratio) was fed to the reaction tube at a feeding ratio of 5.8 g/hr to carry out reaction. WHSV was 0.9hr$^-$and reaction temperature was 350 °C.

The results are shown in Table 10.

TABLE 10

| Time lapsed (hr) | Conversion (%) | Selectivity (%) |
|---|---|---|
| 6.25 | 99.4 | 89.0 |
| 21.25 | 98.4 | 90.8 |
| 31.25 | 97.6 | 89.0 |

EXAMPLE 20

Catalyst I (0.348 g, 0.58 ml) was packed in a quartz glass reaction tube of 1 cm in inner diameter and preheated in nitrogen stream at 350° C. for 1 hour.

Then, a mixed solution of cyclohexanone oxime/methanol (weight ratio)=1/1.86 was fed to the reaction tube in nitrogen stream (4.2/1 hr) at a feeding rate of 8.0 g/hr to carry out reaction. WHSV was 8.0 hr$^{-1}$and reaction temperature was 350° C. Reaction product was trapped and collected under cooling with dry ice-methanol solution every one hour and analyzed by gas chromatography.

The results are shown in Table 11.

TABLE 11

| Time lapsed (hr) | Conversion (%) | Selectivity (%) |
|---|---|---|
| 1.25 | 100 | 94.3 |
| 3.25 | 100 | 91.1 |
| 6.25 | 100 | 93.6 |

Comparative Example 10

Reaction was carried out in the same manner as in Example 20 except that toluene was used in place of the methanol and a mixed solution of cyclohexaonone oxime/toluene=1/1.86 (weight ratio) was fed to the reaction tube at a feeding rate of 8.0 g/hr and the reaction temperature was 350° C. WHSV was 8.0 hr$^-$.

The results are shown in Table 12.

TABLE 12

| Time lapsed (hr) | Conversion (%) | Selectivity (%) |
|---|---|---|
| 1.25 | 98.8 | 75.7 |
| 3.25 | 94.8 | 84.8 |
| 6.25 | 86.7 | 87.1 |

EXAMPLE 21

Catalyst I (0.9 g, 1.5 ml) was packed in a quartz glass reaction tube of 1 cm in inner diameter and was preheated at 350 °C. under reduced pressure (30 Torr. Then, the pressure was adjusted to 80 Torr and a mixed solution of cyclohexanone oxime/methanol=1/5 (weight ratio) was fed to the reaction tube at a feeding rate of 4.8 g/hr to carry out the reaction. WHSV was 0.9 hr$^{-1}$ and reaction temperature was 350 +C. The reaction product was trapped and collected under ice-cooling every one hour and analyzed by gas chromatography.

The results are shown in Table 13.

TABLE 13

| Time lapsed (hr) | Conversion (%) | Selectivity (%) |
|---|---|---|
| 1.25 | 98.8 | 95.1 |
| 3.25 | 98.8 | 95.6 |
| 6.25 | 96.7 | 95.3 |

Comparative Example 11

Reaction was carried out in the same manner as in Example 21 except that toluene was used in place of the methanol and a mixed solution of cyclohexanone oxime/toluene= 1/5 (weight ratio) was fed tot he reaction tube at a feeding rate of 4.8 g/hr and reaction temperature was 350° C.

The results are shown in Table 14.

TABLE 14

| Time lapsed (hr) | Conversion (%) | Selectivity (%) |
|---|---|---|
| 1.25 | 100.0 | 78.5 |
| 3.25 | 99.8 | 84.4 |
| 6.25 | 95.0 | 88.6 |

EXAMPLE 22

Reaction was carried out in the same manner as in Example 21 except that catalyst J was used in place of the catalyst I.

The results are shown in Table 15.

TABLE 15

| Time lapsed (hr) | Conversion (%) | Selectivity (%) |
|---|---|---|
| 1.25 | 99.6 | 95.4 |
| 3.25 | 98.8 | 95.9 |
| 6.25 | 97.6 | 96.2 |

Comparative Example 12

Reaction was carried out in the same manner as in Comparative Example 11 except that catalyst J was used in place of the catalyst I.

Results are shown in Table 16.

TABLE 16

| Time lapsed (hr) | Conversion (%) | Selectivity (%) |
|---|---|---|
| 1.25 | 99.9 | 86.9 |
| 3.25 | 99.6 | 88.7 |
| 6.25 | 97.8 | 90.4 |

EXAMPLE 23

Catalyst B (0.3 g, 0.5 ml) was packed in a quartz glass reaction tube of 1 cm in inner diameter and preheated in a nitrogen stream at 350°C. for 1 hour. Then, a mixed solution of cyclohexanone oxime/methyl tert-butyl ether/benzene=⅓.1/10.6 (weight ratio) was fed to the reaction tube at a feeding rate of 11.5 g/hr to carry out reaction. WHSV was 2.7 hr $^{-1}$ and reaction temperature was 350 ° C. The reaction product was trapped and collected under water-cooling every one hour and analyzed by gas chromatography.

The results are shown in Table 17.

TABLE 17

| Time lapsed (hr) | Conversion (%) | Selectivity (%) | Yield (%) |
|---|---|---|---|
| 1.25 | 98.7 | 82.1 | 81.0 |
| 3.25 | 98.3 | 84.6 | 83.2 |
| 6.25 | 90.6 | 88.6 | 80.3 |

Comparative Example 13

Reaction was carried out in the same manner as in Example 23 except that ether compound was not present in the reaction system and a mixed solution of cyclohexanone oxime/benzene=1/11.5 (weight ratio) was fed to the reaction tube at a feeding rate of 11.5 g/hr (WHSV=3.1).

The results are shown in Table 18.

TABLE 18

| Time lapsed (hr) | Conversion (%) | Selectivity (%) | Yield (%) |
|---|---|---|---|
| 1.25 | 99.8 | 78.1 | 77.9 |
| 3.25 | 98.6 | 79.8 | 78.7 |
| 6.25 | 89.7 | 81.8 | 73.4 |

EXAMPLES 24–26

Reaction was carried out using the same catalyst as used in Example 23 in the same manner as in Example 23 except that ether compounds as shown in Table 19 were used in place of the methyl tert-butyl ether and feeding rate and feed ratio of raw materials as shown in Table 19 were employed. Reaction temperature was 350° C.

The results are shown in Table 19.

TABLE 19

| Example | Ether compound | Feeding[1] ratio | WHSV ($hr^{-1}$) | Time lapsed (hr) | Conversion (%) | Selectivity (%) | Yield (%) |
|---|---|---|---|---|---|---|---|
| 24 | Methyl n-propyl ether | 1/2.6/11.1 | 1.6 | 1.25 | 99.7 | 80.0 | 79.8 |
| | | | | 3.25 | 95.3 | 88.1 | 84.0 |
| 25 | Diethyl ether | 1/2.6/11.1 | 2.6 | 1.25 | 100 | 79.5 | 79.5 |
| | | | | 6.25 | 97.3 | 82.6 | 80.4 |
| 26 | Anisole | 1/7.7/6.1 | 2.8 | 2.25 | 98.5 | 81.7 | 80.5 |
| | | | | 6.25 | 91.9 | 84.1 | 77.3 |

Note:
[1]Ratio of cyclohexanone oxime/ether compound/benzene (weight)

We claim:

1. A process for producing ε-caprolactam which comprises carrying out gas phase reaction of cyclohexanone oxime using a solid acid as a catalyst in the presence of a compound represented by the formula (I):

$$R_1-O-R_2 \quad (I)$$

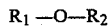

wherein $R_1$ represents a lower alkyl group which may be substituted with a fluorine atom and $R_2$ represents a hydrogen atom, a lower alkyl group or a phenyl group.

2. A process according to claim 1, wherein the compound of the formula (I) is a lower alcohol having a hydrogen atom as $R_2$.

3. A process according to claim 2, wherein the lower alcohol is at least one alcohol selected from the group consisting of methanol, ethanol, n-propanol and isopropanol.

4. A process according to claim 2, wherein the lower alcohol is methanol or ethanol.

5. A process according to claim 2, wherein the lower alcohol is present in an amount of 0.1-20 times as much as the weight of cyclohexanone oxime.

6. A process according to claim 5, wherein the lower alcohol is present in an amount of 0.3-8 times as much as the weight of cyclohexanone oxime.

7. A process according to claim 2, wherein the solid acid as catalyst is crystalline metallosilicate or crystalline silicate.

8. A process according to claim 7, wherein the crystalline metallosilicate has an Si/Me atomic ratio of at least 5 wherein Me represents at least one metallic element selected from the group consisting of Al, Ga, Fe, B, Zn, Cr, Be, Co, La, Ti, Zr, Hf, V, Ni, Sb, Bi, Cu and Nb.

9. A process according to claim 7, wherein the crystalline metallosilicate or crystalline silicate has pentasil type structure.

10. A process according to claim 1, wherein the compound of the formula (I) is an ether compound having a lower alkyl group or a phenyl group as $R_2$.

11. A process according to claim 10, wherein the ether compound is at least one compound selected from the group consisting of dimethyl ether, diethyl ether, methyl n-propyl ether, methyl tert-butyl ether and anisole.

12. A process according to claim 10, wherein the ether compound is present in an amount or 0.1-20 times as much as the weight of cyclohexanone oxime.

13. A process according to claim 12, wherein the ether compound is present in an amount of 0.3-15 times as much as the weight of cyclohexanone oxime.

14. A process according to claim 10, wherein the solid acid as catalyst is crystalline metallosilicate or crystalline silicate.

15. A process according to claim 14, wherein the crystalline metallosilicate has an Si/Me ratio of at least 5 wherein Me represents at least one metallic element selected from the group consisting of Al, Ga, Fe, B, Zn, Cr, Be, Co, La, Ti, Zr, Hf, V, Ni, Sb, Bi, Cu and Nb.

16. A process according to claim 14, wherein the crystalline metallosilicate or the crystalline silicate has pentasil type structure.

* * * * *